(12) United States Patent
Chou et al.

(10) Patent No.: US 7,868,213 B2
(45) Date of Patent: Jan. 11, 2011

(54) 1,4-BIS(BROMODIFLUOROMETHYL) TETRAFLUOROBENZENE AND PRODUCING METHOD THEREOF

(75) Inventors: Chuan-Yu Chou, Jhongli (TW); Po-Chen Chang, Pingjhen (TW); Chun-Hsu Lin, Taipei (TW); Shieh-Jun Wang, Taipei (TW)

(73) Assignees: Yuan-Shin Materials Technology Corp (TW); Chung-Shan Institute of Science and Technology, Armaments Bureau. M.N.D. (TW)

( * ) Notice: Subject to any disclaimer, the term of this patent is extended or adjusted under 35 U.S.C. 154(b) by 283 days.

(21) Appl. No.: 12/219,796

(22) Filed: Jul. 29, 2008

(65) Prior Publication Data

US 2009/0171130 A1    Jul. 2, 2009

(30) Foreign Application Priority Data

Dec. 28, 2007    (TW) .............................. 96150785 A

(51) Int. Cl.
    *C07C 22/00*    (2006.01)
    *C07C 17/20*    (2006.01)

(52) U.S. Cl. ...................................... 570/145; 570/170
(58) Field of Classification Search ................. 570/145, 570/170
    See application file for complete search history.

(56) References Cited

U.S. PATENT DOCUMENTS 7,652,178 B2 *    1/2010    Dolbier et al. .............. 570/126

FOREIGN PATENT DOCUMENTS

JP        2005183729    *    7/2005

* cited by examiner

*Primary Examiner*—Jafar Parsa
(74) *Attorney, Agent, or Firm*—Bacon & Thomas, PLLC

(57) ABSTRACT

A method for producing 1,4-bis(bromodifluoromethyl)tetrafluorobenzene (BFTFB) is disclosed. The target compound is predicted as a very potent monomer for low dielectric constant material. This method comprises the following steps: (a) mixing 1,4-bis(bromodifluoromethyl)tetrafluorobenzene (DFMTFB), a bromination agent, and a solvent (with or without) to form a mixture; (b) heating the mixture under UV radiation; and (c) purifying the resultant to obtain 1,4-bis(bromodifluoromethyl)tetrafluorobenzene (BFTFB) with high purity.

20 Claims, 4 Drawing Sheets

1,4-BIS(BROMODIFLUOROMETHYL) TETRAFLUOROBENZENE AND PRODUCING METHOD THEREOF

BACKGROUND OF THE INVENTION

1. Field of the Invention

The present invention relates to perhalogen-aromatic compounds without any hydrogen atoms and a method for producing the same. More particularly, the present invention relates to 1,4-bis(bromodifluoromethyl)tetrafluorobenzene and a method for producing the same in a high yield.

2. Description of Related Art

Halogen-containing aromatic compounds, especially those have substituted by a difluoroalkyl group or a bromodifluoroalkyl group, their polymerization products have excellent properties such as thermal and chemical resistance, water repellent, low-dielectric constant, low reflectivity and so on.

Recently, among commercial fluorine-containing aromatic compounds, poly(tetrafluoro-p-xylene) represented by the following formula (1) has been widely applied to dielectric films in the electronics and coating industries due to its excellent processability. Products coated with poly(tetrafluoro-p-xylene) have excellent properties such as anticorrosion, moisture-proofness, electrics insulation, and the coating films are ultrathin, transparent, and pinholeless.

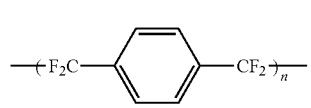

formula (1)

1,4-bis(bromodifluoromethyl)benzene (BFB) represented by the following formula (2) is an important precursor for preparing poly(tetra-fluoro-p-xylene).

formula (2)

BFB is mainly obtained by reacting α,α,α',α'-tetrafluoro-p-xylene (TFPX) with a brominating agent, N-bromosuccinimide (NBS). Currently, the method for synthesizing BFB is to dissolve TFPX and NBS in $CCl_4$ solvent, and then to reflux the mixture under UV irradiation to obtain BFB in a yield of 50 to 80%. Alternatively, BFB also can be obtained by using $Br_2$ instead of NBS to brominating TFPX (for example, the addition of $Br_2$ into the reaction solution was divided in several times at 80° C. under visible-light irradiation of 390 to 500 nm).

Since the dielectric constant of fluorine-containing poly-p-xylene decreases as the amount of fluorine atoms increases in the molecule, the polymer formed from precursor, 1,4-bis(bromodifluoromethyl)tetrafluorobenzene (BFTFB), can predictably have a lower dielectric constant than poly(tetrafluoro-p-xylene).

Commonly, BFTFB can be synthesized in a similar manner of synthesizing BFB, but the starting material for bromination is 1,4-bis(difluoromethyl)tetrafluorobenzene (DFMTFB) instead of TFPX.

However, in the synthesis of BFTFB mentioned above, there are several disadvantages in that: (1) the brominating agent, NBS, decomposes rapidly at high temperature under UV irradiation or initiator condition, and is usually used at reaction temperature below 100° C.; (2) $Br_2$ easily evaporates and loses under reflux at 80° C. due to its low boiling point, hence the amount of $Br_2$ used usually raises to several times more than the theoretical amount thereof and it is difficult to perform the bromination at temperature higher than 80° C.; (3) most polymers and metals can't resist the corrosive effect of bromine, only very limited materials capable of being used as a reactor.

Furthermore, because the starting material, 1,4-bis(difluoromethyl)tetrafluorobenzene (DFMTFB), has four fluorine atoms on benzene ring, the strong electronegativity makes the molecule unusually chemical stable and incapable of being brominated under above-mentioned conventional bromination condition. As a result, it is understood that a higher temperature condition is necessary for provision of higher energy than the conventional method to synthesize 1,4-bis(bromodifluoromethyl)tetrafluorobenzene (BFTFB).

SUMMARY OF THE INVENTION

In view of drawbacks described above, the present invention provides a perfluoroaromatic compound without any hydrogen atoms, which is 1,4-bis(bromodifluoromethyl)tetrafluorobenzene (BFTFB) represented by the following formula (3):

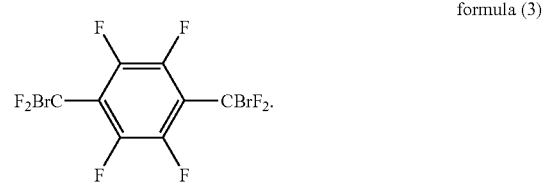

formula (3)

Furthermore, the present invention also provides a method for producing 1,4-bis(bromodifluoromethyl)tetrafluorobenzene, as represented by the following reaction (I):

reaction (I)

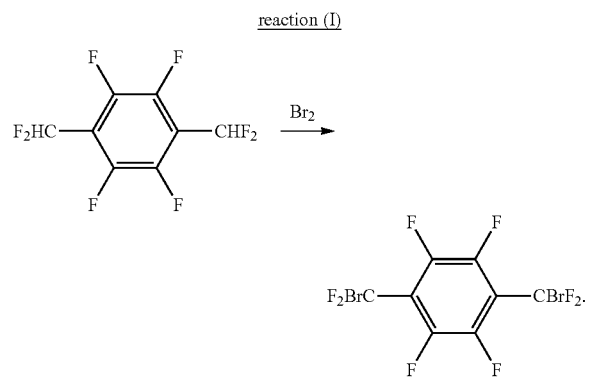

The invention discloses a method for preparation of 1,4-bis(bromodifluoromethyl)tetrafluorobenzene by photo-bromination of 1,4-bis(difluoromethyl)tetrafluorobenzene. As mentioned above, owing to limitations such as the low decomposition temperature of NBS and the low boiling point of $Br_2$, conventional bromination can be performed only at 80° C. or lower reaction temperature, and it is not suitable for production of 1,4-bis(bromodifluoromethyl)tetrafluorobenzene. However, the present invention provides a bromination system which can undergo bromination at 100° C. or higher temperature in a pressurized solvent-free system or in an atmospheric solvent system.

Therefore, the present invention provides a method of producing 1,4-bis(bromodifluoromethyl)tetrafluorobenzene (BFTFB) in a solvent-free system, comprising the following steps:

(a) mixing $Br_2$ and 1,4-bis(difluoromethyl)tetrafluorobenzene (DFMTFB) to form a mixture;

(b) heating the mixture under UV irradiation until the temperature thereof is raised to the range of 100 to 200° C.;

(c) extracting the mixture by a solvent to obtain a reaction solution; and (d) purifying the reaction solution to afford 1,4-bis(bromodifluoromethyl)tetrafluorobenzene.

In the method of the present invention, HBr can be discharged and additional $Br_2$ can be further added into the mixture at a fixed interval of time when the reaction is performed in the step (b), preferably. As a result, 1,4-bis(difluoromethyl)tetrafluorobenzene can be brominated completely, and the pressure of the reactor can be appropriately regulated.

In the method of the present invention, the step (a) can further comprise a process of adding a basic reagent into the mixture to absorb HBr generated during reaction.

The basic reagent can be selected from the group consisting of alkali metal carbonate, alkali metal hydroxide, alkali metal oxide, alkaline-earth metal carbonate, alkaline-earth metal hydroxide, and alkaline-earth metal oxide. Preferably, the basic reagent is sodium carbonate ($Na_2CO_3$), potassium carbonate ($K_2CO_3$), sodium hydroxide (NaOH), potassium hydroxide (KOH), magnesium oxide (MgO), or calcium oxide (CaO).

In the method of the present invention, the reaction time of the step (b) needed can be determined by sampling the solution and analysed by GC. However, if the reaction time is less than 24 hours, the products are in a low yield. If the reaction time is more than 96 hours, the yield of the products is not obviously raised. Hence, the reaction time preferably is from 24 to 96 hours.

In the method of the present invention, the reaction pressure of the step (b) is determined according to the reaction temperature and the amount of $Br_2$ added, and it is preferably from 1 to 10 kg/cm².

In the method of the present invention, if the reaction temperature is less than 100° C., it is not easy to perform bromination; if the reaction temperature is higher than 200° C., gumming occurs easily. Hence, the reaction temperature is preferably in the range of from 100 to 200° C., more preferably between 130 and 180° C.

In the method of the present invention, the molar ratio of $Br_2$ to 1,4-bis(difluoromethyl)tetrafluorobenzene is not limited, but preferably is more than 2:1.

In the method of the present invention, the solvent of the step (c) can be a polar solvent, and preferably is ethyl acetate.

In the method of the present invention, the step (d) can comprise the following steps:

(d1) neutralizing the reaction solution;

(d2) filtrating and concentrating the reaction solution; and (d3) purifying the reaction solution by column chromatography.

Moreover, the present invention further provides a method for producing 1,4-bis(bromodifluoromethyl)tetrafluorobenzene in a solvent system comprising the following steps:

(a) mixing $Br_2$, 1,4-bis(difluoromethyl)tetrafluorobenzene (DFMTFB), and a solvent to form a reaction solution;

(b) heating the reaction solution under UV irradiation until the temperature thereof is raised to the range of 100 to 200° C.; and (c) purifying the reaction solution to afford 1,4-bis(bromodifluoromethyl)tetrafluorobenzene.

In the method of the present invention, additional $Br_2$ can be further added into the reaction solution at a fixed interval of time in the step (b), preferably. As a result, 1,4-bis(difluoromethyl)tetrafluorobenzene can be brominated completely.

In the method of the present invention, the reaction time of the step (b) needed can be determined by sampling the solution and analysed by GC. However, if the reaction time is less than 24 hours, the products are in a low yield. If the reaction time is more that 96 hours, the yield of the products is not obviously raised. Hence, the reaction time preferably is from 24 to 96 hours.

In the method of the present invention, the condition of the reaction solution in the step (b) is not limited under heating. Preferably, the reaction solution can reflux under heating.

In the method of the present invention, if the reaction temperature is less than 100° C., it is not easy to perform bromination; if the reaction temperature is higher than 200° C., gumming easily occurs. Hence, the reaction temperature is preferably in the range of from 100 to 200° C., more preferably between 110 and 180° C.

In the method of the present invention, the molar ratio of $Br_2$ to 1,4-bis(difluoromethyl)tetrafluorobenzene is not limited, but preferably is more than 2:1.

In the method of the present invention, the solvent can be a halogen aliphatics or a halogen aromatics, and preferably is at least one selected from the group consisting of chloropentafluorobenzene ($C_6F_5Cl$), bromopentafluorobenzene ($C_6F_5Br$), o-dichlorobenzene (o-$C_6H_4Cl_2$), and bromotrichloromethane ($CBrCl_3$).

In the method of the present invention, the step (c) can comprise the following steps:

(c11) neutralizing the reaction solution;

(c12) filtrating and concentrating the reaction solution; and (c13) purifying the reaction solution by column chromatography.

DETAILED DESCRIPTION OF THE PREFERRED EMBODIMENT

EXAMPLE 1

Figure 1:
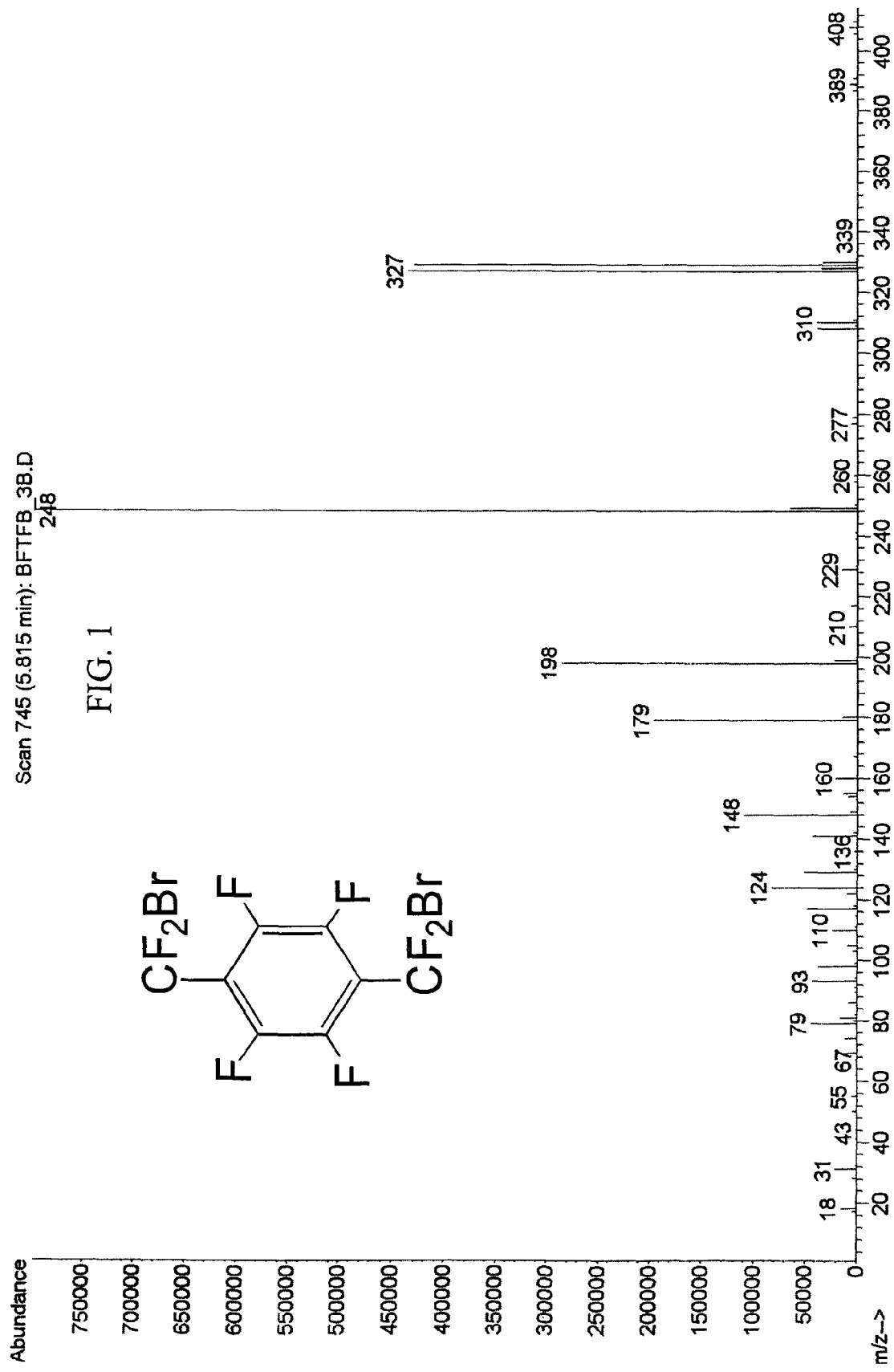
FIG. 1 shows the mass spectrum of 1,4-bis(bromodifluoromethyl)tetrafluorobenzene prepared in Example 1 of the present invention.

Production of 1,4-Bis(bromodifluoromethyl)tetrafluorobenzene in a Solvent-Free Method A 100-ml reaction flask was equipped with a feed tank of $Br_2$ and an exhaustion valve. After the reaction flask was dried by $N_2$, 20 g (0.08 mole) of 1,4-bis(difluoromethyl)tetrafluorobenzene (DFMTFB) and 2 ml (0.04 mole) of $Br_2$ were added into the reaction flask and then stirred evenly. Subsequently, the mixture in the reaction flask was irradiated with a mercury lamp (400 W) and heated to 165° C. so as to perform bromination. HBr generated in the reaction flask during bromination was discharged every 8 hours, and 1.0 ml of $Br_2$ was added into the reaction flask to maintain reaction.

After being irradiated with the mercury lamp for 56 hours, the reaction mixture was cooled. The reaction mixture was dissolved by ethyl acetate and neutralized by 5% alkali solution. Then, the organic solution was analyzed by GC/MS. As a result of analysis, the formation of 1,4-bis(bromodifluoromethyl)tetrafluorobenzene (compound 1) and (1-bromodifluoromethyl-4-difluoromethy)tetrafluorobenzene (compound 2) was confirmed. According to the results of GC analysis, the starting material was exhausted completely, and the GC area percentages of the compound 1 and the compound 2 were 93.1% and 4.3%, respectively.

Finally, the organic solution was neutralized, filtrated, concentrated, and refined by column chromatography with silica gel. 24.1 g of colorless liquid product, 1,4-bis(bromodifluoromethyl)tetrafluorobenzene, was obtained, and its purity and yield were 99.5% and 73.9%, respectively. The DSC (Differential Scanning Calorimetry) analysis of the resultant product shows a peak at 209.4° C. which corresponds to the boiling point of 1,4-bis(bromodifluoromethyl) tetrafluorobenzene. The analysis result is listed as the following.

Figure 2:
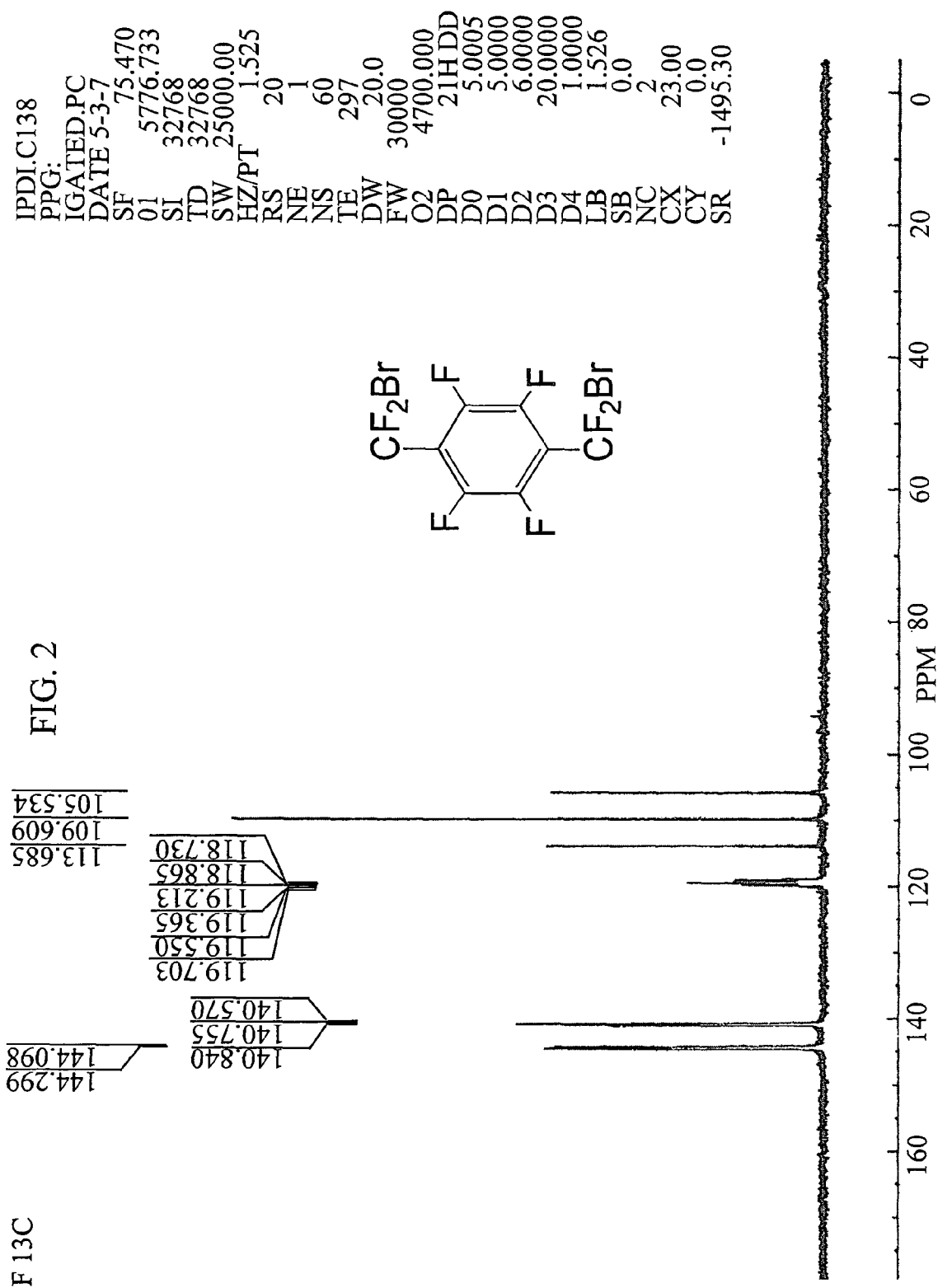
FIG. 2 shows the $^{13}C$ NMR spectrum of 1,4-bis(bromodifluoromethyl)tetrafluorobenzene prepared in Example 1 of the present invention.
Figure 3:
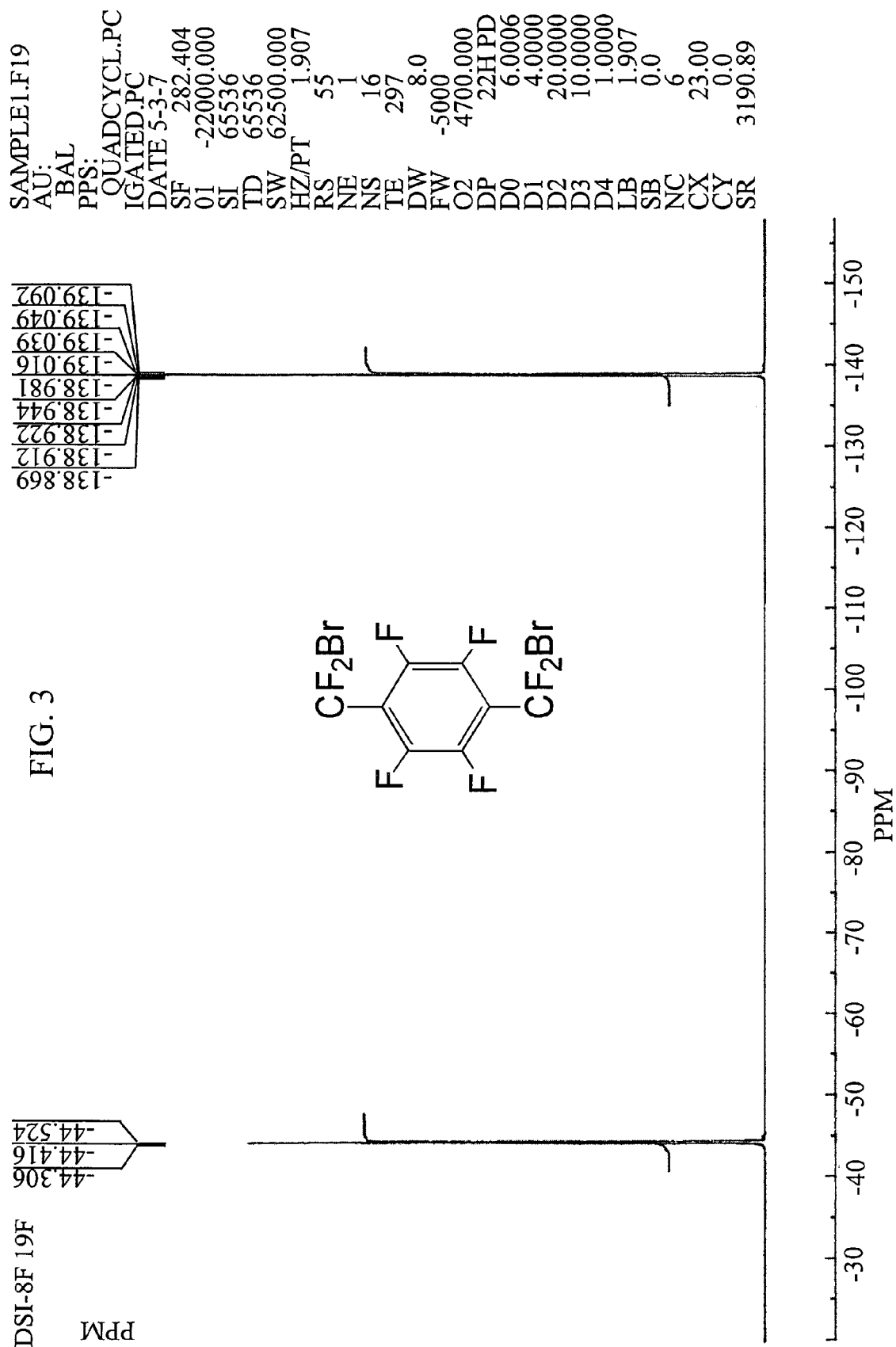
FIG. 3 shows the $^{19}F$ NMR spectrum of 1,4-bis(bromodifluoromethyl)tetrafluorobenzene prepared in Example 1 of the present invention.
Figure 4:
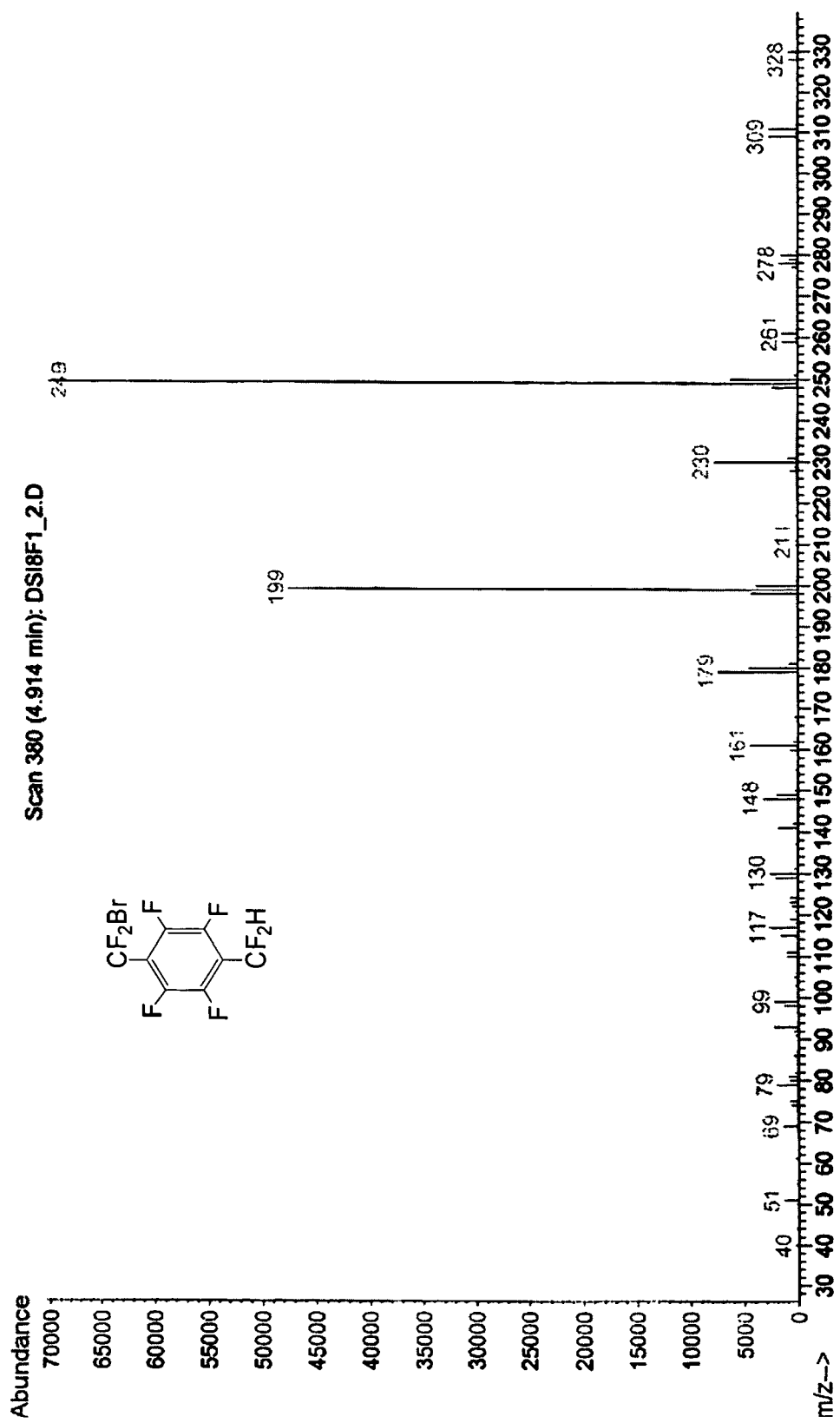
FIG. 4 shows the mass spectrum of (1-bromodifluoromethyl-4-difluoromethyl)tetrafluorobenzene prepared in the example 1 of the present invention.

<The Results of the Chemical Analysis>
1,4-bis(bromodifluoromethyl)tetrafluorobenzene (compound 1)
  (a) Mass spectrum: $C_8Br_2F_8$, $M^+$=408 ( FIG. 1)
  (b) $^{13}C$ NMR($CDCl_3$; external standard: TMS):
    δ (ppm)=109.61 (2C, t), 119.23 (2C, m), 142.43 (4C, dm) (FIG. 2)
  (c) $^{19}F$ NMR ($CDCl_3$; external standard: $CFCl_3$)
    δ (ppm)=−139.37 (4F, m), −44.76 (4F, m) (FIG. 3)
  (e) Element analysis:
    Theoretical value: C=23.6%, H=0.0%, F=37.2%, Br=39.1%
    Experimental value: C=23.6%, H=0.0%, F=37.0%, Br=38.9%
(1-bromodifluoromethyl-4-difluoromethyl)tetrafluorobenzene (compound 2)
  (a) Mass spectrum: $C_8HBrF_8$, $M^+$=329 (FIG. 4)

EXAMPLE 2

Production of
1,4-Bis(bromodifluoromethyl)tetrafluorobenzene in a Solvent-Free Method (HBr Absorbed)

Photo-bromination was performed by following the procedure of Example 1, except MgO was added into the reaction to absorb HBr generated, without discharging HBr during the course of reaction. Addition of basic reagents helped reaction (I) shifting forward to the right according to Lechatelier's principle and further lowered the pressure of the reactor. The reaction steps are listed as follows.

5 g (0.02 mole) of 1,4-bis(difluoromethyl)tetrafluorobenzene (DFMTFB), 2.3 ml (0.044 mole) of $Br_2$, and 1.8 g of MgO were added into a reaction flask and then stirred evenly. Subsequently, the mixture in the reaction flask was irradiated with a mercury lamp (400 W), heated to 165° C. to undergo reaction for 26 hours, and then cooled the reaction mixture to room temperature. The mixture in the reaction flask was dissolved by ethyl acetate, and then the organic solution was sampled to undergo GC/MS analysis. The GC area percentages of 1,4-bis(bromodifluoromethyl) tetrafluorobenzene (compound 1) and (1-bromodifluoromethyl-4-difluoromethyl)tetrafluorobenzene (compound 2) were 91.4% and 2.1%, respectively.

Finally, the reaction solution was neutralized, filtrated, concentrated, and refined by column chromatography with silica gel. 5.7 g of 1,4-bis(bromodifluoromethyl)tetrafluorobenzene was afforded and its purity and yield were 99.1% and 69.9%, respectively.

EXAMPLE 3

Production of
1,4-Bis(bromodifluoromethyl)tetrafluorobenzene in a Solvent Method Besides the starting material 1,4-bis(difluoromethyl)tetrafluorobenzene and the brominating agent ($Br_2$), a solvent was added into the reaction system to undergo reflux bromination at atmospheric pressure in the present example. The reaction steps are listed as follows.

A 50-ml flask was equipped with a feed tank of $Br_2$ and a condenser. After the reaction flask was dried by $N_2$, 20 ml of chloropentafluorobenzene, 5 g (0.02 mole) of 1,4-bis(difluoromethyl)tetrafluorobenzene (DFMTFB) and 1 ml (0.02 mole) of $Br_2$ were added to the reaction flask and then stirred evenly. Subsequently, the mixture in the reaction flask was irradiated with a mercury lamp (400 W) and heated to undergo reflux. 1.0 ml of $Br_2$ was added to the reaction every 8 hours to maintain reaction.

After being refluxed and irradiated with the mercury lamp for 96 hours, the reaction mixture was cooled to room temperature. The reaction solution was neutralized by alkali solution. Then, the organic solution was sampled to undergo gas chromatography. The GC area percentages of 1,4-bis(bromodifluoromethyl)tetrafluorobenzene (compound 1), (1-bromodifluoromethyl-4-difluoromethyl)tetrafluorobenzene (compound 2), and 1,4-bis(difluoromethyl)tetrafluorobenzene were 24.2%, 56.0 and 19.8%, respectively.

EXAMPLES 4-6

Production of
1,4-Bis(bromodifluoromethyl)tetrafluorobenzene in a Solvent Method In addition to chloropentafluorobenzene ($C_6F_5Cl$), other solvents such as bromopentafluorobenzene ($C_6F_5Br$), o-dichlorobenzene ($C_6H_4Cl_2$), and bromotrichloromethane ($CBrCl_3$) were used as the reaction solvent performing bromination reaction under atmospheric pressure. Examples 4-6 were performed approximately in the same manner as Example 3. The solvent, the reaction condition, and the GC results of Examples 3-6 are listed as the following Table 1.

TABLE 1

| Solvent | Reflux Temperature (° C.) | Reaction Time (hours) | Product Conversion Rate Determined by GC Analysis (%) | |
|---|---|---|---|---|
| | | | Compound 1 | Compound 2 |
| $C_6F_5Cl$ | 120~125 | 96 | 24.2 | 56.0 |
| $C_6F_5Br$ | 130~135 | 72 | 8.8 | 46.4 |
| o-$C_6H_4Cl_2$ | 170~180 | 39 | 27.0 | 59.8 |
| $CBrCl_3$ | 115~120 | 36 | 21.8 | 44.3 |

COMPARATIVE EXAMPLE 1

Reaction in an NBS/CCl$_4$ System 20 ml of carbon tetrachloride (CCl$_4$), 5 g (0.02 mole) of 1,4-bis(difluoromethyl)tetrafluorobenzene (DFMTFB) and 8.9 g (0.05 mole) of N-bromosuccinimide (NBS) were added to a 50-ml reaction flask and then stirred evenly. Subsequently, the mixture in the reaction flask was irradiated with a mercury lamp (400 W) and heated to undergo reflux for 48 hours. After that, the mixture was sampled to undergo GC analysis. The GC analysis shows 0.9% of the GC area percentage of (1-bromodifluoromethyl-4-difluoromethyl)tetrafluorobenzene (compound 2), and no 1,4-bis(bromodifluoromethyl)tetrafluorobenzene (compound 1) is detected.

COMPARATIVE EXAMPLE 2

Reaction Without UV Irradiation 50 ml of carbon tetrachloride (CCl$_4$), 2.5 ml of Br$_2$, and 5 g of 1,4-bis(difluoromethyl)tetrafluorobenzene (DFMTFB) were added to a 200-ml autoclave. Subsequently, the mixture was heated to 140° C. for 48 hours. After that, the mixture was sampled to undergo GC analysis. Neither 1,4-bis(bromodifluoromethyl)tetrafluorobenzene (compound 1) nor (1-bromodifluoromethyl-4-difluoromethyl)tetrabenzene (compound 2) was detected.

Although the present invention has been explained in relation to its preferred embodiment, it is to be understood that many other possible modifications and variations can be made without departing from the scope of the invention as hereinafter claimed.

What is claimed is:

1. A method for producing 1,4-bis(bromodifluoromethyl) tetrafluorobenzene comprising the following steps:
    (a) mixing Br$_2$ and 1,4-bis(difluoromethyl)tetrafluorobenzene to form a mixture;
    (b) heating the mixture under UV irradiation until the temperature thereof is raised to the range of 100 to 200°;
    (c) extracting the mixture by a solvent to obtain a reaction solution; and
    (d) purifying the reaction solution to afford 1,4-bis(bromodifluoromethyl) tetrafluorobenzene.

2. The method as claimed in claim 1, wherein HBr is discharged and additional Br$_2$ is further added into the mixture at a fixed interval of time when the reaction is performed in the step (b).

3. The method as claimed in claim 1, wherein the step (a) further comprises a process of adding a basic reagent into the mixture.

4. The method as claimed in claim 3, wherein in the step (a), the basic reagent is selected from the group consisting of alkali metal carbonate, alkali metal hydroxide, alkali metal oxide, alkaline-earth metal carbonate, alkaline-earth metal hydroxide, and alkaline-earth metal oxide.

5. The method as claimed in claim 1, wherein the reaction time of the step (b) is from 24 to 96 hours.

6. The method as claimed in claim 1, wherein the reaction pressure of the step (b) is from 1 to 10 kg/cm$^2$.

7. The method as claimed in claim 1, wherein the reaction temperature of the step (b) is from 130 to 180°.

8. The method as claimed in claim 1, wherein the molar ratio of Br$_2$ to 1,4-bis(difluoromethyl)tetrafluorobenzene is more than 2:1.

9. The method as claimed in claim 1, wherein the solvent of the step (c) is a polar solvent.

10. The method as claimed in claim 9, wherein the solvent is ethyl acetate.

11. The method as claimed in claim 1, wherein the step (d) comprises the following steps:
    (d1) neutralizing the reaction solution;
    (d2) filtrating and concentrating the reaction solution; and
    (d3) purifying the reaction solution by column chromatography.

12. A method for producing 1,4-bis(bromodifluoromethyl) tetrafluorobenzene comprising the following steps:
    (a) mixing Br$_2$, 1,4-bis(difluoromethyl)tetrafluorobenzene, and a solvent to form a reaction solution;
    (b) heating the reaction solution under UV irradiation until the temperature thereof is raised to the range of 100 to 200°; and
    (c) purifying the reaction solution to afford 1,4-bis(bromodifluoromethyl) tetra-fluorobenzene.

13. The method as claimed in claim 12, wherein additional Br$_2$ is further added into the reaction solution at a fixed interval of time when the reaction is performed in the step (b).

14. The method as claimed in claim 12, wherein the reaction time of the step (b) is from 24 to 96 hours.

15. The method as claimed in claim 12, wherein the reaction solution of the step (b) is heated until it undergoes reflux.

16. The method as claimed in claim 12, wherein the reaction temperature of the step (b) is from 110 to 180°.

17. The method as claimed in claim 12, wherein the molar ratio of Br$_2$ to 1,4-bis(difluoromethy)tetrafluorobenzene is more than 2:1.

18. The method as claimed in claim 12, wherein the solvent is a halogen aliphatics or a halogen aromatics.

19. The method as claimed in claim 18, wherein the solvent is at least one selected from the group consisting of chloropentafluorobenzene (C$_6$F$_5$Cl), bromo-pentafluorobenzene (C$_6$F$_5$Br), o-dichlorobenzene (o-C$_6$H$_4$Cl$_2$), and bromotrichloro-methane (CBrCl$_3$).

20. The method as claimed in claim 12, wherein the step (c) comprises the following steps:
    (c11) neutralizing the reaction solution;
    (c12) filtrating and concentrating the reaction solution; and
    (c13) purifying the reaction solution by column chromatography.

* * * * *